United States Patent [19]

Sutton et al.

[11] Patent Number: 5,086,143
[45] Date of Patent: Feb. 4, 1992

[54] COPOLYMERS CONTAINING POLYOXYALKYLENE SIDE CHAINS

[75] Inventors: Richard C. Sutton; Marsha B. Oenick, both of Rochester, N.Y.

[73] Assignee: Eastman Kodak Company, Rochester, N.Y.

[21] Appl. No.: 557,338

[22] Filed: Jul. 25, 1990

[51] Int. Cl.$^5$ .................. C08F 220/26; C08F 228/02; C08F 12/08; C08F 12/16; C08F 220/18
[52] U.S. Cl. .................... 526/320; 526/286; 526/293; 526/346; 526/329.2; 524/817; 524/825
[58] Field of Search .......... 526/320, 286, 293; 524/817, 825

[56] References Cited

U.S. PATENT DOCUMENTS

| | | | |
|---|---|---|---|
| 3,983,001 | 9/1976 | Coupek et al. | 195/66 R |
| 4,138,381 | 2/1979 | Chang et al. | 524/765 |
| 4,170,582 | 10/1979 | Mori et al. | 524/531 |
| 4,275,138 | 6/1981 | Kita et al. | 430/157 |
| 4,304,591 | 12/1981 | Mueller et al. | 71/93 |
| 4,370,460 | 1/1983 | Neubert et al. | 526/329.2 |
| 4,401,765 | 8/1983 | Craig et al. | 436/533 |
| 4,424,311 | 1/1984 | Nagaoka et al. | 525/303 |
| 4,618,448 | 10/1986 | Cha et al. | 252/180 |

OTHER PUBLICATIONS

Shalaby et al., *Polymers as Biomaterials*, Plenum Press, pp. 361-374 (1984).

Primary Examiner—Joseph L. Schofer
Assistant Examiner—Wu C. Cheng
Attorney, Agent, or Firm—J. Lanny Tucker

[57] ABSTRACT

Copolymers are prepared from (a) at least about 0.5 mole % of monomers having reactive groups which are, directly or indirectly, capable of reaction with free amine or sulfhydryl groups of biologically active substances, (b) from about 0.1 to about 20 mole % of monomers having polyoxyalkylene side chains, each of which side chains has a molecular weight of at least about 88, and (c) up to about 99.4 mole % of oleophilic monomers which provide hydrophobicity to the copolymers. The copolymers can be supplied as latex particles in aqueous compositions.

15 Claims, No Drawings

COPOLYMERS CONTAINING POLYOXYALKYLENE SIDE CHAINS

RELATED APPLICATION

Reference is made to copending and commonly assigned U.S. Ser. No. 558,272, filed on even date herewith by Sutton and Oenick and entitled "Biologically Active Reagent, Analytical Element and Methods for Use of the Reagent".

FIELD OF THE INVENTION

This invention relates to new copolymers which can be used in various analytical and diagnostic methods, and to copolymers useful for affinity chromatography.

BACKGROUND OF THE INVENTION

There is a continuing need in medical practice and research, and in analytical and diagnostic procedures for rapid and accurate determinations of chemical and biological substances which are present in various fluids, such as biological fluids. For example, the presence of drugs, narcotics, hormones, steroids, polypeptides, metabolites, toxins, viruses, microorganisms or nucleic acids in human or animal body fluids or tissues must be determined rapidly and accurately for effective research, diagnosis or treatment.

In approximately the last twenty years, a wide variety of analytical methods have been developed to detect the substances noted above. Generally, the state of the art has advanced to such a degree that analytical and diagnostic methods have become highly reliable, and suitable for automation or for use with test kits which can be readily used in doctors' offices or at home. Most of such methods rely on what are known in the art as "specific binding" reactions in which an unknown substance to be detected (known as a "ligand") reacts specifically and preferentially with a corresponding "receptor" molecule. Most well known specific binding reactions occur between immunoreactants, such as antibodies and antigens (foreign substances which produce immunological responses).

Methods in the art using the specific binding reactions generally require that one or more or both of the reactants be immobilized on a solid substrate of some type, so that unreacted (and generally water-soluble) materials can then be separated from the water-insoluble reaction product (often called a "complex"). In addition, such immobilized reactants can be used in affinity chromatography to remove a desired biologically active material from a mixture of such materials.

Biologically active substances have thus been immobilized to advantage on particulate substrates such as polymeric particles, animal and human erythrocytes, bacterial cells and other materials known in the art. For example, carrier particles prepared from epoxy-group containing monomers are described in U.S. Pat. No. 4,415,700 (issued Nov. 15, 1983 to Batz et al). Carboxylated latex particles have also been used to prepare diagnostic reagents, as noted in U.S. Pat. No. 4,181,636 (issued Jan. 1, 1980 to Fischer). Where polymeric particles have been used as carrier substrates, biologically active substances have been attached through reactive groups on the particle surface, such groups provided either from the polymer composition or from linking moieties attached to the particles. U.S. Pat. No. 4,401,765 (issued Aug. 30, 1983 to Craig et al) describes a number of reactive groups on polymeric particles.

Several advances in the art in this regard are described in EP-A-0 323 692 (published July 12, 1989), EP-A-0 302 715 (published Feb. 8, 1989), and EP-A-0 308 235 (published Apr. 26, 1989). These publications describe various means for attaching biologically active substances to polymeric particles having various reactive surface groups.

U.S. Pat. No. 3,983,001 (issued Sept. 28, 1976 to Coupek et al) describes the use of hydrophilic macroporous copolymers as carriers for biologically active compounds in the preparation of affinity chromatography reagents. Such copolymers can be prepared from certain hydrophilic monomers such as polyglycol acrylates and methacrylates. Biologically active compounds are adsorbed to the carrier polymers. Adsorption, however, does not provide for optimum sensitivity or efficiency in affinity chromatography.

The modification of protein adsorption on polymeric surfaces has been a common goal for many workers trying to apply polymer technology to in vivo and in vitro uses in biotechnology. Undesirable protein adsorption has been a continual problem. For example, nonspecific adsorption is a major concern in the use of polymers for affinity chromatography for the purification of proteins.

The modification of polymer surfaces has taken many forms, including physical coatings, graft copolymerization, chemical treatments and plasma gas discharge treatment. The hydrophilic nature of the polymer surface has been the subject of considerable debate and research because an increase in hydrophilicity reduces adsorption of some proteins, but not others. As noted in the art cited above, the use of reactive side chains has also received considerable attention in the art. However, if the polymer particles are too hydrophilic and swell in aqueous solutions (as in U.S. Pat. No. 3,983,001, noted above), the assays can be adversely affected.

One technique commonly used to reduce nonspecific adsorption of proteins is what is called "capping". After a desired protein (for example, an antibody) is covalently attached to polymeric particles, another nonimmunoreactive protein is allowed to adsorb to the particle surface to "cap" the remaining reactive sites. While this is generally effective in some cases, it would be desirable to avoid this step because of the expense and extra time it requires for preparing useful reagents. Thus, there is a continuing need for polymers which can be used to immobilize desired biologically active substances without the need for "capping" and where non specific interactions are considerably reduced or eliminated entirely.

SUMMARY OF THE INVENTION

The need in the art noted above is met with a water-insoluble copolymer having recurring units derived from:

(a) at least about 0.5 mole % of one or more ethylenically unsaturated polymerizable monomers having reactive groups which are, directly or indirectly, capable of reaction with free amine or sulfhydryl groups of biologically active substances, (b) from about 0.1 to about 20 mole % of one or more ethylenically unsaturated polymerizable monomers having polyoxyalkylene side chains, each of which side chains has a molecular weight of at least about 88, and (c) up to about 99.6 mole % of one or more ethylenically unsaturated polymerizable oleophilic monomers which provide hydrophobicity to the copolymer.

Also provided by this invention is an aqueous latex composition which comprises particles having, on at least the outer surface thereof, the water-insoluble copolymer described above, the particles being present at from about 0.5 to about 50 weight percent of the composition.

These polymers are useful for the preparation of biologically active reagents, and in a variety of analytical and diagnostic procedures, including the medical, analytical and methods described in more detail in U.S. Ser. No. 558,272 filed on even date herewith by Sutton et al (noted above). The reagents can also be used in affinity chromatography, as described in the noted copending application. The copolymers of this invention are advantageous in such uses because of the presence of polyoxyalkylene side chains extending from the polymer which reduce nonspecific protein adsorption. Each of these side chains has a molecular weight of at least about 88.

DETAILED DESCRIPTION OF THE INVENTION

The copolymers of this invention have as an essential component recurring units derived from one or more ethylenically unsaturated polymerizable monomers having polyoxyalkylene side chains of a specific molecular weight. These monomers are identified as those in the (b) component of the definition of the copolymers provided herein. A mixture of monomers can be used if desired.

Each polyoxyalkylene side chain generally has a molecular weight of from about 88 to about 1350. Such side chains can have linear or branched alkylene groups of 2 to 4 carbon atoms, and if there is more than one of such groups in a given monomer, they can be the same or different. Preferably, each monomer contains one such alkylene group.

More specifically, these monomers are represented by the structure (I):

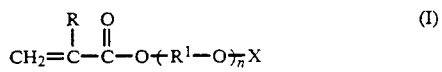

wherein R is hydrogen or methyl, and $R^1$ is alkylene having 2 to 4 carbon atoms (such as ethylene, propylene, trimethylene, n-butylene or iso-butylene). X is hydrogen or acyl (such as acetyl, propionyl, benzoyl or butyryl), and n is 2 to 30.

Preferably, R is hydrogen or methyl, $R^1$ is an alkylene having 2 to 3 carbon atoms (branched or linear), X is hydrogen and n is 2 to 20.

Representative monomers [component (b)] of the copolymer include, but are not limited to, pentaethylene glycol monomethacrylate, decaethylene glycol monomethacrylate, eicosaethylene glycol monomethacrylate, pentaethylene glycol monoacrylate, polypropylene glycol monomethacrylate and polypropylene glycol monoacrylate. The preferred monomers include pentaethylene glycol monomethacrylate, decaethylene glycol monomethacrylate and polypropylene glycol monomethacrylate, with the first two being more preferred.

The critical monomers described above are copolymerized with two other types of ethylenically unsaturated polymerizable monomers to provide the copolymers of this invention.

In one embodiment, the (a) monomers have reactive groups which are, directly or indirectly, capable of reaction with free amine or sulfhydryl groups of biologically active substances, and the (c) monomers are oleophilic to provide additional hydrophobicity to the copolymer.

There are many polymerizable monomers which have the reactive groups necessary for reaction with biologically active substances. These reactive groups can be directly reacted with the biologically active substances, or indirectly reacted through linking moieties or through intermediates which are created during attachment of the biologically active substances to the particles. A mixture of monomers having the same or different reactive groups can be used if desired.

Representative reactive groups include carboxy, active halogen, activated 2-substituted ethylsulfonyl, activated 2-substituted ethylcarbonyl, active ester, vinylsulfonyl, vinylcarbonyl, aldehyde, epoxy, amino (after activation) and sulfhydryl and others which would be readily apparent to one skilled in the art.

Following are some monomers listed by representative useful reactive groups. This list is not intended to be limiting in any manner.

CARBOXY

Useful monomers include acrylic acid and methacrylic acid, itaconic acid, aconitic acid, fumaric acid, maleic acid, $\beta$-carboxyethyl acrylate, $\beta$-carboxyethyl methacrylate, m & p-carboxymethylstyrene, methacrylamidohexanoic acid, N-(2-carboxy-1,1-dimethylethyl)acrylamide and salts and anhydride precursors thereof.

Particularly useful monomers having reactive carboxy groups are described in copending U.S. Ser. No. 539,768 (filed June 18, 1990 by Ponticello and Sutton).

ACTIVE HALOGENS

Examples of useful monomers include vinyl chloroacetate, vinyl bromoacetate, haloalkylated vinyl aromatics (such as chloromethylstyrene and bromomethylstyrene), haloalkyl acrylic or methacrylic esters (such as chloroethyl methacrylate, 3-chloro-2-hydroxypropyl methacrylate and 3-chloropropyl acrylate), N-{3-[N'-(3-chloropropionyl)ureido]propyl}methacrylamide, 4-(3-chloropropionyl)ureidostyrene, 4-[N'-(3-chloropropionyl)ureido]styrene, 2-(3-chloropropionamido)ethyl methacrylate, N-[3-(3-chloropropionamido)propyl]methacrylamide, N-(3-chloroacetamidopropyl)methacrylamide, N-(2-chloroacetamidoethyl)methacrylamide, 4-chloroacetamidostyrene, 4-chloroacetamidomethylstyrene, N-[3-(N'-chloroacetylureido)propyl]methacrylamide, N-[2-(N'-chloroacetylureido)ethyl]methacrylamide, 4-(N'-chloroacetylureido)styrene, and m- & p-(N'chloroacetylureidomethyl)styrene. Chloromethylstyrene is most preferred.

ACTIVATED 2-ETHYLSULFONYL AND VINYLSULFONYL

A number of monomers having these groups are described in U.S. Pat. No. 4,161,407 (issued July 7, 1979 to Campbell) and U.S. Pat. No. 4,548,870 (issued Oct. 22, 1985 to Ogawa et al). Preferred monomers can be represented by the formula (II):

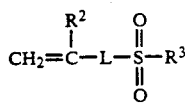

wherein R² is hydrogen or substituted or unsubstituted alkyl (generally of 1 to 6 carbon atoms, such as methyl, ethyl, isopropyl or hexyl). Preferably, R² is hydrogen or methyl.

R³ is —CH=CHR⁴ or —CH₂CH₂Y wherein Y is a leaving group which is displaced by a nucleophile or is eliminated in the form of HY by treatment with a base (such as halo, acetoxy, alkylsulfonyloxy such as methylsulfonyloxy, arylsulfonyloxy such as p-tolylsulfonyloxy, trialkylammonio, for example, a trimethylammonio salt or pyridinio salt). R⁴ is hydrogen, substituted or unsubstituted alkyl (generally of 1 to 6 carbon atoms as defined for R²), or substituted or unsubstituted aryl (generally of 6 to 12 nuclear carbon atoms, such as phenyl, naphthyl, xylyl or tolyl). Preferably, R³ is —CH₂CH₂Y. This group, which is an activated 2-substituted ethyl group, can be substituted with any group which does not impair the displacement of the leaving group Y.

L is a linking group which can be a substituted or unsubstituted alkylene generally having 1 to 20 carbon and hetero atoms in the backbone. This definition of alkylene is meant to include alkylene groups interrupted or terminated with oxy, thio, —NR⁵— [wherein R⁵ hydrogen, substituted or unsubstituted alkyl of 1 to 6 carbon atoms (such as methyl, chloromethyl or 2-hydroxyethyl) or substituted or unsubstituted aryl of 6 to 10 carbon atoms (such as phenyl, napthyl or xylyl)], ester (—COO—), amide (—CONH—), urylene

sulfonyl (—SO₂—), carbonate, sulfonamido, azo, phosphono or other similar groups. Representative alkylene groups include methylene, ethylene, isobutylene, hexamethylene, carbonyloxyethyleneoxycarbonylethylene, methylenebis(iminocarbonyl)ethylene, carbonyloxydodecylenecarbonyloxyethylene, carbonyliminomethyleneiminocarbonyliminoethylene, carbonyliminomethyleneiminocarbonylethylene and other groups described or suggested by U.S. Pat. No. 4,161,407 and U.S. Pat. No. 4,548,870 (noted above).

L can also be substituted or unsubstituted arylene generally having 6 to 12 nuclear carbon atoms. Representative arylene groups include phenylene, tolylene, naphthalene and others noted in the patents mentioned above. Also included in this definition of L are divalent groups which are combinations of one or more of each of the alkylene and arylene groups defined above (for example, arylenealkylene, alkylenearylenealkylene and others readily determined by one of ordinary skill in the art), as well as such combinations which are interrupted or terminated by one or more amide or ester groups (for example, carbonyliminoarylenealkylene). Preferably, L is substituted or unsubstituted phenylenealkylene [for example, substituted with one or more alkyl groups (as defined for R²), alkoxy groups (generally of 1 to 6 carbon atoms, for example, methoxy, propoxy or butoxy) or halo groups], carbonyliminoarylenealkylene (wherein arylene and alkylene are defined above), or carbonyliminoalkyleneiminocarbonylalkylene (wherein alkylene are defined above).

Representative useful monomers include, but are not limited to , m- & p-(2-chloroethylsulfonylmethyl)styrene, m- & p-[2-(p-tolylsulfonyloxy)ethylsulfonylmethyl]styrene, m- & p-vinylsulfonylmethylstyrene, N-[m- & p-(2-chloroethylsulfonylmethyl)phenyl]acrylamide, and N-[2(2-chloroethylsulfonyl)ethylformamidomethyl]acrylamide. The first monomer is preferred.

ALDEHYDE

Useful monomers include acrolein, p-methacryloyloxybenzaldehyde, 4-vinylbenzaldehyde, N-formyl-2-aminoethyl acrylate, p-formylphenyl methacrylate and others readily apparent to one skilled in polymer chemistry such as those described in U.S. Pat. No. 3,625,694 (issued Dec. 7, 1971 to Cohen et al).

EPOXY

Monomers with epoxy groups include glycidyl methacrylate, glycidyl acrylate, vinyl glycidyl ether, methallyl glycidyl ether and other readily apparent to one skilled in polymer chemistry.

ACTIVE ESTERS

Useful monomers having active ester groups are described, for example, in U.S. Pat. No. 4,548,870 (issued Oct. 22, 1985 to Ogawa et al).

In addition to the monomers described above, the copolymers of this invention also include recurring units of ethylenically unsaturated polymerizable oleophilic monomers (c) which provide desired hydrophobicity to the copolymers, A mixture of monomers can be used if desired. Such monomers would include, but are not limited to, generally, vinyl aromatics (for example, styrene and styrene derivatives such as 4-vinyltoluene, α-methylstyrene, 2,5-dimethylstyrene, 4-t-butylstyrene and 2-chlorostyrene), acrylic and methacrylic acid esters and amides (for example, methyl acrylate, methyl methacrylate, n-butyl acrylate, 2-ethylhexyl methacrylate, benzyl acrylate and N-phenylacrylamide), butadiene, acrylonitrile, vinyl acetate, vinylbenzyl acetate, vinyl bromide, vinylidene chloride and crosslinkable monomers having two or more polymerizable groups. Useful crosslinkable monomers include, but are not limited to, divinylbenzene, allyl acrylate and di- and triacrylates and methacrylates (such as 2,2-dimethyl-1,3propylene diacrylate, 1,4-cyclohexylenedimethylene dimethacrylate, ethylene diacrylate, ethylene dimethacrylate propylene diacrylate, propylene dimethacrylate, ethylidyne trimethacrylate) and others readily apparent to one skilled in polymer chemistry.

Preferably, copolymers of this invention are composed of recurring units derived from about 0.5 to about 20 mole % of (a), from about 0.1 to about 20 mole % of (b), and from about 60 to about 99.6 mole % of (c). Most preferred copolymers are prepared from about 1 to about 10 mole % of (a), from about 1 to about 10 mole % of (b), and from about 80 to about 98 mole % of (c).

The copolymers of this invention are prepared using standard emulsion or suspension polymerization techniques, as described for example by Sorenson et al in *Preparative Methods of Polymer Science*, 2nd Ed. (1968), Wiley and Sons, New York, and by Stevens, *Polymer Chemistry, An Introduction*, Addison Wesley Publishing Co., London, 1975, although there are certain preferred conditions which are discussed below. The monomers used to prepare the copolymers are generally available from a number of commercial sources, including Eastman Kodak Company, Dow Chemical, duPont, Alcolac Chemical Co. and Scientific Polymer Products Inc. Other monomers not commercially available are readily prepared by a skilled organic chemist using known procedures and readily available starting materials.

Suspension polymerization procedures are well known and generally involve mechanically dispersing the monomers in a liquid, usually water, and polymerizing the monomer droplets formed from the dispersing action. Polymerization initiators which are soluble in the monomer are generally used, and surfactants can also be used. Small particles of polymer are obtained with careful control of the polymerization conditions, which particles can be isolated using filtration, centrifugation or spray drying.

The polymers of this invention are preferably prepared using emulsion polymerization techniques. In emulsion polymerization (whether batch, continuous or semi-continuous modes as known in the art), it is preferred that the copolymers be prepared as small particles without the use of surfactants (also known as emulsifiers) or colloidal dispersing agents because residual surfactant on the particles tend to interfere with attachment of biologically active substances (for example, antibodies and enzymes). Thus, the resulting latex is substantially free of surfactants and colloidal dispersing agents. Conditions for surfactant-free polymerization is known in the art, for example as described in U.S. Pat. No. 4,415,700 (noted above) and *Research Disclosure* publication 15963 (July, 1977), both incorporated herein by reference. *Research Disclosure* is a publication available from Kenneth Mason Publications, Ltd., The Old Harbourmasters's, 8 North Street, Emsworth, Hampshire PO10 7DD, England. Continuous polymerization is the most preferred technique whereby monomers are added to a reaction vessel over a period of time, as described in more detail in the noted *Research Disclosure* publication.

Some general conditions for emulsion polymerization include reaction of the monomers in the presence of water-soluble, free radical polymerization initiators (such as redox combinations of persulfates and bisulfites including potassium persulfate, ammonium persulfate, potassium bisulfite and sodium bisulfite and others known in the art) in an amount of from about 0.1 to about 5 weight % over a period of from about 30 to about 1200 minutes at a temperature of from about 30 to about 95° C. Other conditions include the use of chain transfer agents such as dodecanethiol at concentrations of from about 0.05 to about 5 weight % (based on monomer weight).

Representative preparations of copolymers useful in this invention are provided in Examples 1–10 below.

The resulting copolymers are generally in small particulate form (predominantly spherical) having an average diameter of from about 0.01 to about 50 μm. Preferably, the particles have an average diameter of from about 0.05 to about 20 μm, and more preferably from about 0.1 to about 10 μm. The water-insoluble particles are generally nonporous and nonswellable in water or water-miscible solvents (such as alcohols), but they are also generally water-dispersible due to their small size. Polymerization generally results in from about 0.5 to about 50 percent solids of copolymer, although, the latex compositions of this invention can have from about 0.5 to about 25 (preferably from about 1 to about 20) percent solids of copolymer particles when used.

Representative copolymers of this invention are: poly[styrene-co-m- & p-(2-chloroethylsulfonylmethyl)styrene-co-pentaethylene glycol monomethacrylate] (90.5:4.5:5 molar ratio), poly(styrene-co-m- & p-chloromethylstyrene-co-pentaethylene glycol monomethacrylate) (85:10:5 molar ratio), poly(styrene-co-m- & p-chloromethylstyrene-co-decaethylene glycol monomethacrylate) (85:10:5 molar ratio), poly(styrene-co-m- & p-chloromethylstyrene-co-polypropylene glycol monomethacrylate) (85:10:5 molar ratio), poly[styrene-co-m- & p-(2-chloroethylsulfonylmethyl)styrene-co-pentaethylene glycol monomethacrylate] (94.5:4.5:1 molar ratio), poly[styrene-co-m- & p-(2-chloroethylsulfonylmethyl)styrene-co-pentaethylene glycol monomethacrylate-co-divinylbenzene] (93.5:4.5:1:1 molar ratio), poly[styrene-co-m- & p-(2-chloroethylsulfonylmethyl)styrene-co-decaethylene glycol monomethacrylate] (90.5:4.5:5 molar ratio), poly[styrene-co-m- & p-(2-chloroethylsulfonylmethyl)styrene-co-decaethylene glycol monomethacrylate-co-divinylbenzene] (93.5:4.5:1:1 molar ratio), poly[styrene-co-m- & p-(2-chloroethylsulfonylmethyl)styrene-co-pentaethylene glycol monomethacrylate] (90.5:4.5:5 molar ratio), poly[styrene-co-m- & p-(2-chloroethylsulfonylmethyl)styrene-co-pentaethylene glycol monomethacrylate-co-ethylene glycol dimethacrylate] (89.5:4.5:5:1 molar ratio), poly(styrene-co-m- & p-chloromethylstyrene-co-polypropylene glycol monomethacrylate) (85:10:5 molar ratio), and poly[styrene-co-m- & p-(2-chloroethylsulfonylmethyl)styrene-co-pentaethylene glycol monomethacrylate] (79.5:0.5:20 molar ratio).

The polymeric particles described herein can have a detectable marker distributed throughout the particle or within a portion thereof. Such markers can include colorimetric or fluorometric dyes, radioisotopes or other detectable materials that can be incorporated within the particles. The markers can be incorporated by attaching them to the polymerizable monomers, followed by polymerization as described herein. Alternatively and preferably, dyes can be incorporated using procedures described in more detail in U.S. Pat. No. 4,199,363 (issued Apr. 22, 1980 to Chen), U.S. Pat. No. 4,259,313 (issued Mar. 31, 1981 to Frank et al) and EP-A-0 308 233 (noted above).

While in most cases, the copolymers of this invention are formed as homogeneous particles, that is, the particles are composed of the same copolymer throughout, it is essential that at least the outer surface of the particles be composed of a copolymer of this invention. Particles having an outer shell of the copolymer can be prepared by graft copolymerization or other known procedures whereby an already formed particle is coated with a copolymer described herein.

In one embodiment, the copolymers of this invention can be used to prepare what are known in the art as core-shell polymer particles. In these materials, the core is prepared from a polymer different from the shell polymer. For example, the core can be any water-insoluble vinyl addition polymer latex particle. The shell of the particles could be prepared from a copolymer of this invention while the core is prepared from a different polymer (whether of this invention or not). Methods of making core-shell polymer particles are well known in the art, for example U.S. Pat. No. 4,401,765 (issued Aug. 30, 1983 to Craig et al) and EP-A-0 280 556 (published Aug. 31, 1988). Generally, the shell polymer comprises from about 20 to about 70, and preferably from about 30 to about 60, weight percent of the total core-shell weight. Core-shell particles are often used in agglutination or other assays for diagnostic purposes. For example, such particles can have a detectable marker (such as a dye) incorporated within their cores for use in agglutination assays. The marker can be incorporated using techniques known in the art, such as the those described in EP-A- 0 308 233 (noted above).

Generally, core-shell polymers are prepared using staged emulsion polymerization procedures. Emulsion polymerization of the core is carried to substantial completion by continuously adding reactants to a reaction vessel under standard conditions. Monomers and catalysts needed to make the shell polymer are then continuously added to the vessel containing the latex of the core polymer. In this manner, the shell has a definite known composition rather than being a mixture of core and shell monomers. Representative details of preparations are provided in EP-A-0 280 556 (noted above).

The following examples are provided to illustrate, and not to limit, the scope of this invention. The starting materials are commercially available unless otherwise noted. All percentages are by weight, unless otherwise indicated.

EXAMPLES 1-10

PREPARATION OF VARIOUS COPOLYMERS

These examples illustrate the preparation of several copolymers of this invention using a continuous, surfactant-free emulsion polymerization method. The procedure is described for the copolymer of Example 1, but is generally the same for each copolymer except where noted.

The following copolymers were prepared:

Example 1: Poly(styrene-co-m- & p-chloromethylstyrene-co-pentaethylene glycol monomethacrylate ) (85:10:5 molar ratio), Example 2: Poly[styrene-co-m- & p-chloromethylstyrene co-poly(propylene glycol) monomethacrylate] (85:10:5molar ratio), Example 3: Poly[styrene co-m- & p-chloromethylstyrene-co-poly(decaethylene glycol) monomethacrylate] (85:10:5 molar ratio), Example 4: Poly[styrene-co- m- & p-(2-chloroethylsulfonylmethyl)styrene-co-poly(pentaethylene glycol) monomethacrylate] (90.5:4.5:5 molar ratio), Example 5: Poly[styrene-co-m- & p-(2-chloroethylsulfonylmethyl)styrene-co-poly(propylene glycol) monomethacrylate] (90.5:4.5:5 molar ratio), Example 6: Poly(styrene-co-m- & p-(2-chloroethylsulfonylmethyl)styrene-co-poly(decaethylene glycol) monomethacrylate] (90.5:4.5:5 molar ratio), Example 7: Poly(styrene-co-m- & p-(2-chloroethylsulfonylmethyl)styrene-co-poly(pentaethylene glycol) monomethacrylate-co-m- & p-divinylbenzene] (93.5:4.5:1:1 molar ratio), Example 8: Poly[styrene-co-m- & p-(2-chloroethylsulfonylmethyl)styrene-co-poly(decaethylene glycol) monomethacrylate-co-divinylbenzene] (93.5:4.5:1:1 molar ratio), Example 9: Poly[styrene-co-acrylic acid-co-poly(-decaethylene glycol) monomethacrylate] (85:10:5 molar ratio), Example 10: Poly[styrene-co-acrylic acid-co-poly(-pentaethylene glycol) monomethacrylate] (89:5:6 molar ratio).

GENERAL POLYMERIZATION PROCEDURE

Three solutions of reagents were simultaneously added and mixed in a reaction vessel at 80° C. Solution 1 contained all of the monomers styrene (376.39 g), m- & p-chloromethylstyrene (64.72 g) and pentaethylene glycol monomethacrylate (65.14 g), and 1-dodecanethiol (5.06 g). Solution 2 contained ammonium peroxydisulfate (10.13 g) in distilled water (1012.5 g). Solution 3 contained sodium pyrosulfite (5.06 g) in distilled water (1012.5 g).

The three solutions were pumped into the reaction vessel at the following individual rates: Solution 1 at 1.2 g/min., Solution 2 at 2.3 g/min. and Solution 3 at 2.2 g/min. After an addition time of 375 minutes, the reaction was stopped, and the yield was about 1120 g at 18.4% solids. The copolymer latex was then dialyzed for 4 days to remove impurities with a resulting % of solids of 12.25 and a pH of about 4.5. The average particle size was about 0.25 μm, as determined by photon correlation spectroscopy using a Brookhaven Instruments Corporation Instrument equipped with a Model BI-200SM goniometer, a BI-2030 digital correlator and a Jodan 15 mW He-Ne laser. Elemental analysis of the copolymer indicated a molar ratio of about 85:10:5.

The invention has been described in detail with particular reference to preferred embodiments thereof, but it will be understood that variations and modifications can be effected within the spirit and scope of the invention. Moreover, all patents, patent applications (published or unpublished, foreign or domestic), literature references or other publications noted above are incorporated herein by reference for any disclosure pertinent to the practice of this invention.

We claim:

1. A water-insoluble, nonporous particulate copolymer having recurring units derived from:
   (a) from about 0.5 to about 20 mole % of one or more ethylenically unsaturated polymerizable monomers having reactive groups which are, directly, or indirectly, capable of reaction with amino or sulfhydryl groups of biologically active substances,
   the reactive groups selected from the group consisting of carboxy, active halogen, activated 2-substituted ethylsulfonyl, activated 2-substituted ethylcarbonyl, active ester, vinylsulfonyl, vinylcarbonyl, aldehyde, epoxy, amino and sulfhydryl,
   (b) from about 0.1 to about 20 mole % of one or more ethylenically unsaturated polymerizable monomers having polyoxyalkylene side chains, each of which side chains has a molecular weight of at least about 88, and
   (c) from about 60 to about 99.4 mole % of one or more ethylenically unsaturated polymerizable vinyl aromatic monomers which provide hydrophobicity to said copolymer.

2. The copolymer of claim 1 having recurring units derived from:
   from about 1 to about 10 mole % of the (a) monomers,
   from about 1 to about 10 mole % of the (b) monomers, and
   from about 80 to about 98 mole % of the (c) monomers.

3. The copolymer of claim 1 wherein the (b) monomers are represented by the structure (I):

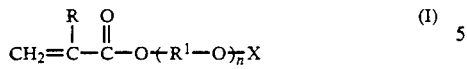

wherein R is hydrogen or methyl, $R^1$ alkylene having 2 to 4 carbon atoms, X is hydrogen or acyl and n is 2 to 30.

4. The copolymer of claim 3 wherein $R^1$ is alkylene having 2 or 3 carbon atoms, X is hydrogen, and n is 2 to 20.

5. The copolymer of claim 1 wherein the (b) monomers are pentaethylene glycol monomethacrylate, decaethylene glycol monomethacrylate and polypropylene glycol monomethacrylate.

6. The copolymer of claim 1 selected from the groups consisting of: poly[styrene-co-m- & p-(2-chloroethylsulfonylmethyl)styrene-co-pentaethylene glycol monomethacrylate] (90.5:4.5:5 molar ratio), poly(styrene-co-m- & p-chloromethylstyrene-co-pentaethylene glycol monomethacrylate) (85:10:5 molar ratio), poly(styrene-co-m- & p-chloromethylstyrene-co-decaethylene glycol monomethacrylate) (85:10:5 molar ratio), poly(styrene-co-m- & p-chloromethylstyrene-co-polypropylene glycol monomethacrylate) (85:10:5 molar ratio), poly[styrene-co-m- & p-(2-chloroethylsulfonylmethyl)styrene-co-pentaethylene glycol monomethacrylate] (94.5:4.5:1 molar ratio), poly[styrene-co-m- & p-(2-chloroethylsulfonylmethyl)styrene-co-pentaethylene glycol monomethacrylate-co-divinylbenzene] (93.5:4.5:1:1 molar ratio), poly[styrene-co-m- & p-(2-chloroethylsulfonylmethyl)styrene-co-decaethylene glycol monomethacrylate] (90.5:4.5:5 molar ratio), poly[styrene-co-m- & p-(2-chloroethylsulfonylmethyl)styrene-co-decaethylene glycol monomethacrylate-co-divinylbenzene] (93.5:4.5:1:1 molar ratio), poly[styrene-co-m- & p-(2-chloroethylsulfonylmethyl)styrene-co-pentaethylene glycol monomethacrylate] (90.5:4.5:5 molar ratio), poly[styrene-co-m- & p-(2-chloroethylsulfonylmethyl)styrene-co-pentaethylene glycol monomethacrylate-co-ethylene glycol dimethacrylate] (89.5:4.5:5:1 molar ratio), poly(styrene-co-m- & p-chloromethylstyrene-co-polypropylene glycol monomethacrylate) (85:10:5 molar ratio), and poly[styrene-co-m- & p-(2-chloroethylsulfonylmethyl)styrene-co-pentaethylene glycol monomethacrylate] (79.5:0.5:20 molar ratio).

7. An aqueous latex composition comprising particles having, at least on the outer surface thereof, a water-insoluble copolymer having recurring units derived from:
(a) from about 0.5 to about 20 mole % of one or more ethylenically unsaturated polymerizable monomers having reactive groups which are, directly, or indirectly, capable of reaction with amino or sulfhydryl groups of biologically active substances, the reactive groups selected from the group consisting of carboxy, active halogen, activated 2-substituted ethylsulfonyl, activated 2-substituted ethylcarbonyl, active ester, vinylsulfonyl, vinylcarbonyl, aldehyde, epoxy, amino and sulfhydryl.
(b) from about 0.1 to about 20 mole % of one or more ethylenically unsaturated polymerizable monomers having polyoxyalkylene side chains, each of which side chains has a molecular weight of at least about 88, and
(c) from about 60 to about 99.4 mole % of one or more ethylenically unsaturated polymerizable vinyl aromatic monomers which provide hydrophobicity to said copolymer, the particles being present at from about 0.5 to about 50 weight percent of said composition.

8. The composition of claim 7 which is substantially free of surfactants and colloidal dispersing agents.

9. The composition of claim 7 wherein said copolymeric particles have an average diameter of from about 0.01 to about 50 μm.

10. The composition of claim 7 wherein said copolymer has recurring units derived from about 1 to about 10 mole % of (a) monomer, from about 1 to about 10 mole % of (b) monomer and from about 80 to about 98 mole % of (c) monomer.

11. The composition of claim 7 wherein the (b) monomers are represented by the structure (I):

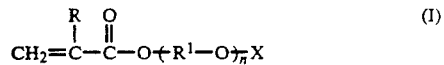

wherein R is hydrogen or methyl, $R^1$ is alkylene having 2 to 4 carbon atoms, X is hydrogen or acyl and n is 2 to 30.

12. The composition of claim 7 wherein said copolymer is selected from the group consisting of: poly[styrene-co-m- & p-(2-chloroethylsulfonylmethyl)styrene-co-pentaethylene glycol monomethacrylate] (90.5:4.5:5 molar ratio), poly(styrene-co-m- & p-chloromethylstyrene-co-pentaethylene glycol monomethacrylate) (85:10:5 molar ratio), poly(styrene-co-m- & p-chloromethylstyrene-co-decaethylene glycol monomethacrylate) (85:10:5 molar ratio), poly(styrene-co-m- & p-chloromethylstyrene-co-polypropylene glycol monomethacrylate) (85:10:5 molar ratio), poly[styrene-co-m- & p-(2-chloroethylsulfonylmethyl)styrene-co-pentaethylene glycol monomethacrylate] (94.5:4.5:1 molar ratio), poly[styrene-co-m- & p-(2-chloroethylsulfonylmethyl)styrene-co-pentaethylene glycol monomethacrylate-co-divinylbenzene] (93.5:4.5:1:1 molar ratio), poly[styrene-co-m- & p-(2-chloroethylsulfonylmethyl)styrene-co-decaethylene glycol monomethacrylate] (90.5:4.5:5 molar ratio), poly[styrene-co-m- & p-(2-chloroethylsulfonylmethyl)styrene-co-decaethylene glycol monomethacrylate-co-divinylbenzene] (93.5:4.5:1:1 molar ratio), poly[styrene-co-m- & p-(2-chloroethylsulfonylmethyl)styrene-co-pentaethylene glycol monomethacrylate] (90.5:4.5:5 molar ratio), poly[styrene-co-m- & p-(2-chloroethylsulfonylmethyl)styrene-co-pentaethylene glycol monomethacrylate-co-ethylene glycol dimethacrylate] (89.5:4.5:5:1 molar ratio), poly(styrene-co-m- & p-chloromethylstyrene-co-polypropylene glycol monomethacrylate) (85:10:5 molar ratio), and poly[styrene-co-m- & p-(2-chloroethylsulfonylmethyl)styrene-co-pentaethylene glycol monomethacrylate] (79.5:0.5:20 molar ratio).

13. The composition of claim 7 wherein said particles are present at from about 0.5 to about 25 weight percent of said composition.

14. The composition of claim 7 wherein said particles are core-shell polymer particles wherein the shell is composed of said water-insoluble copolymer and comprises from about 20 to about 70 weight percent of the total core-shell weight.

15. The composition of claim 14 wherein said core-shell particle has a detectable marker in its core.

* * * * *